United States Patent
Rigg

(10) Patent No.: US 11,690,928 B2
(45) Date of Patent: Jul. 4, 2023

(54) FRAGRANCE DELIVERY SYSTEMS

(71) Applicant: Peter Rigg, Middlesex, NJ (US)

(72) Inventor: Peter Rigg, Middlesex, NJ (US)

( * ) Notice: Subject to any disclaimer, the term of this patent is extended or adjusted under 35 U.S.C. 154(b) by 443 days.

(21) Appl. No.: 16/024,053

(22) Filed: Jun. 29, 2018

(65) Prior Publication Data

US 2019/0015540 A1  Jan. 17, 2019

Related U.S. Application Data

(60) Provisional application No. 62/533,279, filed on Jul. 17, 2017.

(51) Int. Cl.
*A61L 9/12* (2006.01)

(52) U.S. Cl.
CPC ........... *A61L 9/12* (2013.01); *A61L 2209/131* (2013.01)

(58) Field of Classification Search
CPC ....... A61L 9/12; A61L 9/125; A61L 2209/131
See application file for complete search history.

(56) References Cited

U.S. PATENT DOCUMENTS

| | | | | |
|---|---|---|---|---|
| 4,285,468 A | * | 8/1981 | Hyman | A01M 1/2044 239/55 |
| 4,605,165 A | * | 8/1986 | Van Loveren | A01M 1/2055 239/56 |
| 4,734,278 A | | 3/1988 | Pougalan et al. | |
| 6,255,268 B1 | * | 7/2001 | Counts | C11D 3/3955 252/187.1 |
| 6,745,950 B1 | * | 6/2004 | Longo | A01M 31/008 239/145 |
| 2006/0032937 A1 | | 2/2006 | Caserta et al. | |
| 2007/0272895 A1 | * | 11/2007 | Scialla | A61L 9/04 252/187.21 |
| 2011/0180621 A1 | | 7/2011 | Gruenbacher et al. | |
| 2016/0120986 A1 | * | 5/2016 | Anderson | A61K 9/0024 424/443 |

OTHER PUBLICATIONS

DSM Engineering Materials, Arnitel VT3108, https://plasticsfinder.com/datasheet/Arnitel%C2%AE%20VT3104/X92RW (Year: 2020).*
Sammes et al, High Moisture Vapor Transmission Thermoplastic Polyurethanes, Noveon Inc, 2002.
DSM, Arnitel TPE-E Product Brochure, DSM Engineering Plastics, 2003.
Arkema, Pebax for Breathable Application, Product Slides, 2016.

* cited by examiner

*Primary Examiner* — Christopher R Dandridge
(74) *Attorney, Agent, or Firm* — Milton L. Honiq

(57) ABSTRACT

A fragrance delivery system which includes a container with reservoir compartment and having an outer wall at least partially formed of a fragrance permeable plastic, the plastic being a thermoplastic elastomer block copolymer having a Volume Resistivity from $1\times10^{12}$ to $1\times10^{20}$ Ohms·cm and a Water Absorption from 4 to 20%; and a fragrance composition held within the reservoir, the composition being a mixture of low and high volatile perfume ingredients.

15 Claims, 1 Drawing Sheet

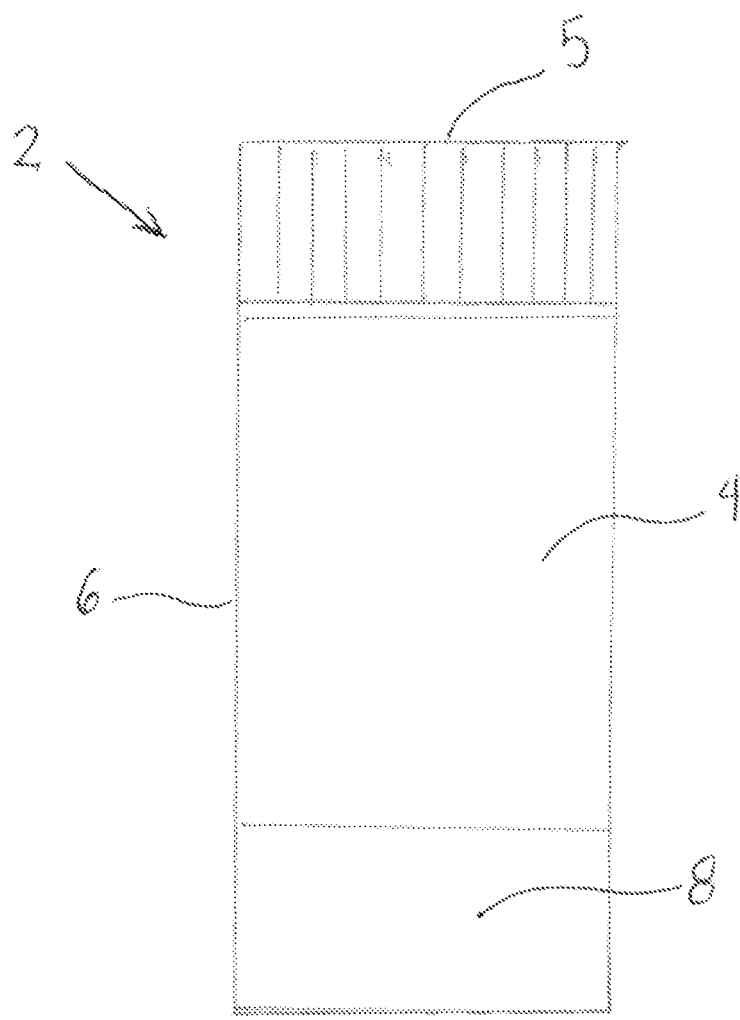

FRAGRANCE DELIVERY SYSTEMS

BACKGROUND OF THE INVENTION

Field of the Invention

The invention relates to systems for more uniformly delivering into a space fragrances having both relatively high-volatile and low-volatile fragrance components.

The Related Art

Many devices are known to release pleasant scents into surrounding open space. Some devices are powered by electrical energy, some by human intervention such as aerosol spray containers, and some by passive diffusion through a barrier wall.

A problem with many of the devices is that high-volatile perfume ingredients exit the device before the low-volatile perfume ingredients. It is difficult to find constructions, particularly plastic containers that allow both small and large molecular weight perfume ingredients to simultaneously escape at a uniform and steady rate. Plastics that allow fragrance to escape are either too porous permitting all ingredients to rapidly escape or too non-porous preventing escape of larger molecules. These problems are addressed and remedied by the present invention.

The Known Art

U.S. Pat. No. 4,734,278 (Pougalan et al) discloses a shaped volatiles emitting body. Perfume is incorporated into the walls of a thermoplastic polyamidic resin of polyether-ester-amide, the resin forming the body.

US Patent Application Publication 2006/0032937A1 (Caserta et al) describes a container for diffusing actives such as fragrances. An important element is a breathable membrane to control homogeneous evaporation of liquid from the container. No chemical description or product name provides any further information on the membrane structure.

US Patent Application Publication 2007/0272895 (Scialla et al) reports a deodorizing system formed as a moisture permeable, water impervious sachet. Perfume is incorporated through hot processing into a plastic mixture forming the sachet thereby becoming intimate with the plastic but releasable to reduce malodors. Amongst the disclosed plastics are Arnitel®, Hytrel®, Pebax® and Estane® all referred to as polar thermoplastic elastomers.

US Patent Application Publication 2011/0180621A1 (Gruenbacher et al) discloses an apparatus for delivering a volatile material in a continuous manner. A breathable membrane encloses a reservoir storing the volatile material. Exempletive of the membrane is Daramic V5 identified as an ultra-high molecular weight microporous polyethylene.

SUMMARY OF THE INVENTION

A fragrance delivery system is herein provided which includes:
  a) a container with at least one reservoir compartment, the container having an outer wall at least partially being formed of a fragrance permeable plastic;
    i) the plastic being a thermoplastic elastomer block copolymer;
    ii) the plastic having a Volume Resistivity ranging from $1\times10^{12}$ to $1\times10^{20}$ Ohms·cm; and
    iii) the plastic having a Water Absorption ranging from 4 to 20%; and
  b) a fragrance composition held within the at least one reservoir compartment, the composition being a mixture of: (1) high volatile perfume ingredients having a boiling point lower than 250° C.; and (2) low volatile perfume ingredients having a boiling point higher than 250° C.

BRIEF DESCRIPTION OF THE DRAWING

FIG. 1 is a side plan view of a container illustrating one embodiment for holding a fragrance composition.

DETAILED DESCRIPTION OF THE INVENTION

Now I have discovered a system for continuously delivering a fragrance composition that simultaneously transmits both low and high volatile perfume ingredients to a space outside the system. A first feature of the system as illustrated in FIG. 1 is a closed container 2 with at least one reservoir compartment 4 secured by a cap closure 5. The at least one reservoir compartment communicates with outer walls 6 of the container. Perfume ingredients of the fragrance compositions 8 can escape the reservoir compartments through the communication channels reaching the outer walls which are formed at least partially of certain select fragrance permeable plastics.

Containers according to the invention can be produced in many different ways. Known techniques include blow molding, co-blow molding, injection molding, co-injection molding, extrusion molding, co-extrusion molding, extrusion coating or injection over-molding. Illustrative containers are wide or narrow mouth capped bottles and jars. Both the cap closures and bottle/jar body can be wholly manufactured from a fragrance permeable plastic. Alternatively, the cap closure or the bottle/jar is made of the permeable plastic while the other is made of a less expensive non-permeable plastic such as polyethylene or polypropylene. In one variation, the bottle is formed of a non-permeable plastic while the closure is formed of the fragrance permeable plastic. In one embodiment, when the container sits upright, perfume ingredients may exit the closure. The exit path can, at a consumer's option, be curtailed by inverting the container to rest on it's closure (i.e. upside down). Thereby the rest surface and closure block emission of perfume ingredients.

A second embodiment utilizes an adhesive backed seal covering the fragrance permeable outer wall (e.g. cap) until ready for use. The seal is formed of a non-permeable plastic such as polyethylene or polypropylene.

In a still further embodiment, the fragrance permeable plastic may be in film form. For instance, the film may be stretched across a mouth of the container (e.g. bottle) to serve as an outer wall. A fragrance non-permeable plastic closure may be employed as a cover for storage purposes. The film may but need not have thickness dimensions ranging from 0.01 to 2 mm, or from 0.1 to 1.5 mm, or even from 0.2 to 1 mm.

Operative plastics advantageously should possess certain physical properties. Surprisingly, we found electrical parameters to be important, For instance, the plastic Volume Resistivity best ranges from $1\times10^{12}$ to $1\times10^{20}$ Ohms·cm, and particularly from $1\times10^{13}$ to $1\times10^{16}$ Ohms·cm. These values are in accordance with Test Method IEC 60093. Dielectric Constant values at 1 MHz can range from 4 to 10, particularly from 4.4 to 5.5 in accordance with Test Method IEC 60250. By contrast, thermoplastics such as polybutylene terephthalate and polyethylene terephthalate have dielectric constants respectively of 3.1 and 3.0. Polyethylene and polyamide (nylon 6) have dielectric constants respectively of 2.3 and 3.6.

Another advantageous defining physical property of the plastic is a Water Absorption ranging from 4 to 20%, and particularly from 6 to 15% as measured per Test Method ISO 62. Further, the plastics utilized herein may have a Moisture Vaporization Transfer Rate (MVTR) of between 500 and 15,000 g/m$^2$/day and sometimes between 1000 and 5000 g/m$^2$/day. The MVTR is measured according to ASTM E96BW at 38° C., 50% relative humidity with a film thickness of 15 um.

An important category of plastic for use herein are thermoplastic elastomer block copolymers. Illustrative of the category are polybutylene-terephthalates copolymerized with at least one block of polyether or at least one block of polyester or at least one block of polyesterether. These plastics are often referred to as thermoplastic copolyester based elastomers with acronym of TPE. Suitable commercially available TPE plastics can be found among some of the Arnitel® (sold by DSM) branded products.

Members of the TPE plastic group have the properties of combining the strength and processing characteristics of engineering plastics with the performance of thermoset elastomers. Attractive for the present invention is that the select TPEs can be hot processed via extrusion molding, injection molding and blow molding. Thus, bottles with outer walls can be formed having at least partial sections of TPE construction.

Advantageously, TPE block-copolymers may contain a polybutylene terephthalate (PBT) hard block and one or more soft blocks of polyether, polyester, and/or polyesterether. The polyether blocks usually have internal repeating units derived from at least one alkylene glycol. The alkylene group generally contains 2-6 carbon atoms, preferably 2-4 carbon atoms. Suitable alkylene glycols are ethylene glycol, propylene glycol and in particular butylene glycol. An illustrative polyether is poly(tetramethyleneoxide).

Polyesters illustratively are derived from the self condensation of alkylene carbonate. Polyhexamethylenecarbonate is a good example. Herein a polycarbonate is understood to be a polyester. Also polyesters may be derived from condensation of an alkylene glycol with an aliphatic dicarboxylic acid. Polyethylene oxide (PEO) or a combination of polyethylene oxide and polypropylene oxide (PEO-PPO-PEO) can be used as the soft block.

The ratio of the soft and hard blocks in the TPE thermoplastic elastomers may generally vary within a wide range dependent on the structure and size (e.g. thickness) of the requisite outer walls. Ratios of soft to hard polymer blocks could range from 1:1 to 1:100, or from 100:1 to 1:1 respectively. Repeating units within any block may range from 2 to 40, sometimes from 2 to 10.

Fragrance compositions described herein normally are a mixture of: (1) high volatile perfume ingredients having a boiling point lower than 250° C.; and (2) low volatile perfume ingredients having a boiling point higher than 250° C. Relative amounts of high to low volatile perfume ingredients may range from 100:1 to 1:2, sometimes from 10:1 to 2:1 by weight respectively.

Non-limiting examples of high volatile perfume ingredients include allo-ocimene, allyl caproate, allyl heptoate, amyl propionate, anethol, anisole, benzaldehyde, benzyl acetate, benzyl acetone, benzyl alcohol, benzyl butyrate, benzyl formate, benzyl propionate, beta gamma hexenol, camphene, camphor, carvacrol, laevo-carvedl, d-carvone, laevo carvone, citral (neral), citronellol, citronellyl acetate, citronellyl nitrile, citronellyl propionate, cuminic aldehyde, Cyclal C, cyclohexyl ethyl acetate, decyl aldehyde, dihydro myrcenol, dimethyl benzyl carbinol, dimethyl octanol, ethyl acetate, ethyl aceto acetate, ethyl amyl ketone, ethyl benzoate, ethylbutyrate, ethylhexyl ketone, ethyl phenyl acetate, eucalyptol, fenchyl acetate, fenchyl alcohol, flor acetate (tricyclo decenyl acetate), frutene (tricyclo decenyl propionate), gamma methyl ionone, gamma-nomalactone, geraniol, geranyl acetate, geranyl formate, geranyl isobutyrate, geranyl nitrile, hexenol, hexenyl acetate, cis-3-hexenyl acetate, hexenyl isobutyrate, cis-3-hexenyl tiglate, hexyl acetate, hexyl formate, hexyl neopentanoate, hexyl tiglate, hydratropic alcohol, hydroxycitronellal, isoamyl alcohol, alpha-ionone, beta-ionone, gamma-ionone, isobornyl acetate, isobutylbenzoate, isomenthol, isomenthone, isononyl acetate, isononyl alcohol, para-isopropyl phenylacetaldehyde, isopulegol, isopulegyl acetate, isoquinoline, Ligustral, d-limonene, linalool, linalool oxide, linalyl acetate, linalyl formate, menthone, menthyl acetate, methyl acetophenone, methyl amyl ketone, methyl anthranilate, methylbenzoate, methylbenzyl acetate, methyl chavicol, methyl eugenol, methylheptenone, methyl heptene carbonate, methyl heptyl ketone, methyl hexyl ketone, alpha-iso "gamma" methyl ionone, methyl nonyl acetaldehyde, methyl octyl acetaldehyde, methyl phenyl carbinyl acetate, methyl salicylate, myrcene, neral, nerol, neryl acetate, nonyl acetate, nonyl aldehyde, octalactone, octyl alcohol (octanol-2), octyl aldehyde, para-cresol, para-cresyl methyl ether, para-cymene, para-methyl acetophenone, phenoxy ethanol, phenyl acetaldehyde, phenyl ethyl acetate, phenyl ethyl alcohol, phenyl ethyl dimethyl carbinol, alpha-pinene, beta-pinene, prenyl acetate, propylbutyrate, pulegone, rose oxide, safrole, alpha-terpinene, gamma-terpinene, 4-terpinenol, alpha-terpineol, terpinolene, terpinyl acetate, tetrahydro linalool, tetrahydro myrcenol, undecenal, veratrol, verdox, vertenex, viridine, and mixtures thereof.

Non-limiting examples of low volatile perfume ingredients include allyl cyclohexane propionate, ambret-15 tolide, amyl benzoate, amyl cinnamate, amyl cinnamic aldehyde, amyl cinnamic aldehyde dimethyl acetal, isoamyl salicylate, aurantiol, benzophenone, benzyl salicylate, cadinene, cedrol, cedryl acetate, cinnamyl cinnamate, coumarin, cyclohexyl salicylate, cyclamen aldehyde, dihydro isojasmonate, diphenyl methane, ethylene brassylate, ethyl methyl phenyl glycidate, ethyl undecylenate, iso-eugenol, exaltolide, galaxolide, geranyl anthranilate, hexadecanolide, hexenyl salicylate, hexyl cinnamic aldehyde, hexyl salicylate, linalyl benzoate, 2-methoxy naphthalene, methyl cinnamate, methyl dihydrojasmonate, beta-methyl naphthyl ketone, musk indanone, musk ketone, musk tibetine, myristicin, delta nomalactone, oxahexadecanolide-10, oxahexadecanolide-11, patchouli alcohol, phantolide, phenyl ethyl benzoate, phenyl ethylphenylacetate, alpha-santalol, thibetolide, delta-undecalactone, gamma-undecalactone, vanillin, vetiveryl acetate, yara-yara, and mixtures thereof.

In the perfume art, some materials having no scent or very faint scent are used as diluents or extenders. Non-limiting examples of these materials are dipropylene glycol, diethyl phthalate, triethyl citrate, isopropyl myristate, and benzyl benzoate. These materials are used for, e.g., diluting and stabilizing some other perfume ingredients. For purposes of this invention, these materials are not counted as "low or high volatile perfume ingredients".

Volatilizable perfume ingredients within the reservoirs will normally constitute from 5 to 100%, sometimes from 20 to 95%, and often 50 to 90% of the liquid in these compartments. Unlike scented consumer products (e.g. laundry detergent, personal cleansers, cosmetics, etc) containing not more than about 1% perfume ingredients, the fragrance compositions described herein serve as their sole function to be a perfume product. Moreover, the perfume ingredients are not impregnated into the plastics either during plastics processing (e.g. hot temperature molding) or at any time subsequent to plastics processing. Outer walls of the containers or reservoirs are not perfume ingredient impregnated. The fragrance permeable plastic of these walls do not store but serve merely to transmit perfume ingredients from the fragrance composition to space outside the outer walls.

The fragrance permeable plastics according to the invention may contain one or more additives such as stabilizers, anti-oxidants, antimicrobial agents, biostatic/biocidal agents, colorants, fillers, binders, fibers, meshes, surface active agents, foaming agents, processing aids, plasticizers, and any other known processing or benefit agents.

The fragrance permeable plastics according to the invention can be applied in multi component molding, for example, two component (2K) molding, either with other fragrance permeable plastics, hybrid metal or other polymers. Multi component molding makes it possible to produce designs comprising hard and soft parts, or parts with different properties.

Except in the examples, or where otherwise explicitly indicated, all numbers in this description indicating amounts of material or conditions of reaction, physical properties of materials and/or use are to be understood as modified by the word "about." All amounts are by weight of the compositions, unless otherwise specified.

It should be noted that in specifying any range of concentration or amount, any particular upper concentration can be associated with any particular lower concentration or amount.

For the avoidance of doubt, the word "comprising" is intended to mean "including" but not necessarily "consisting of" or "composed of." In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

EXAMPLE 1

A set of experiments were conducted to determine fragrance movement across various thermoplastics elastomer block copolymers engineered for their porous breathable constructions. Resin A was Arnitel® TPE type identified by the manufacturer DSM with the designation PL380 (and in extrusion form as VT-3104). Resin B was a TPU polyether thermoplastic urethane copolymer manufactured by Lubrizol designated as Estane® 58315. Resins C and D were Polyether Block Amides manufactured by Arkema designated respectively as Pebax® MV1074 and MV3000. Pebax 2533, mentioned in some literature has been superseded by the Pebax® MV1074 and MV3000 variants.

TABLE I

| Fragrance Release (g) | | | |
| --- | --- | --- | --- |
| VT3104 | 58315 | MV1074 | MV3000 |
| 1.2 | 0.45 | 0.3 | 0.55 |

The test utilized polyethylene bottles having reservoir compartments of 29.6 ml internal volume. A reservoir compartment of each bottle was filled with 10 grams of a standard lavender fragrance composition. Thereafter, the bottle was sealed with an injection molded cap press fit over the open mouth of each bottle. The caps were formed from the resins identified in Table I. Surface area of the cap was 1.4 in$^2$ (9.0 cm$^2$) and wall thickness was 0.03 inches (0.76 mm). The charged bottles were allowed to stand at 72° F. in a ventilated space. They were weighed initially and at the end of 19 days. Loss of fragrance was calculated in grams as reported under Table I. The best release was exhibited with the VT3104 resin formed cap.

Based on these tests, I conclude it is not the breathability or permeability that is a controlling factor. There is a window of properties required of the resin to achieve not only a fragrance release but also a continuous steady emission into space outside the container.

Pebax® 2533 resin was similarly molded into caps. When fragrance liquid was poured into the Pebax 2533 bottle, the molded cap experienced massive swelling; evidently the fragrance liquid was immediately absorbed into the walls with plasticizing effect. The resin was inoperative for purposes of the present invention.

EXAMPLE 2

Various physical properties of the resins under Example 1 were measured (or obtained from the literature). Under the electrical parameters were Volume Resistivity (Test Method IEC 60093) and Dielectric Constant at 1 MHz (Test Method IEC 60250). Under the water vapor parameters were Water Absorption (Test Method ISO 62) and Water Vapor Transmission Rate (MVTR) (Test Method ASTM E96BW). Data are recorded in Table II.

TABLE II

| Physical Properties of the Resins | | | | | |
| --- | --- | --- | --- | --- | --- |
| Property | VT3104 | 58315 | MV1074 | MV3000 | 2533 |
| Volume Resistivity (Ohms · cm) | $1 \times 10^{15}$ | $1.3 \times 10^{11}$ | $2.5 \times 10^9$ | na | $1 \times 10^{10}$ |
| Dielectric Constant | 4.4 | 4.9 | na | na | 6.0 |
| Water Absorption(%) | 7 | 3 | 48 | 28 | 1.2 |
| Water Vapor Transmission Rate | 6000 | na | 19000 | 19000 | na |

By coupling the performance results under Table I with the physical properties under Table II, we can now identify resins that will have utility and success for the present invention. For instance, a Volume Resistivity of greater than $1 \times 10^{12}$ and a Water Absorption no less than 4 or higher than 20% define a window of effective resins.

While the present compositions and methods have been described with reference to the specific variations thereof, it should be understood by those skilled in the art that various changes may be made and equivalents may be substituted without departing from the true spirit and scope of the compositions and methods described herein. In addition, many modifications may be made to adapt a particular situation, material, composition of matter, process, process step or steps, to the objective, spirit and scope of the compounds and methods described herein. All patents and publications cited above are hereby incorporated by reference.

What is claimed is:

1. A fragrance delivery system comprising:
   a) a container with at least one reservoir compartment, the container having an outer wall at least partially being formed of a fragrance permeable plastic;
      i) the plastic being a thermoplastic elastomer block copolymer;
      ii) the plastic having a Volume Resistivity ranging from $1\times10^{12}$ to $1\times10^{20}$ Ohms·cm; and
      iii) the plastic having a Water Absorption ranging from 4 to 20%; and
   b) a fragrance composition held within the at least one reservoir compartment, the composition being a mixture of: (1) high volatile perfume ingredients having a boiling point lower than 250° C.; and (2) low volatile perfume ingredients having a boiling point higher than 250° C.; and wherein the system simultaneously transmits both the high and low volatile perfume ingredients at a uniform and steady rate to space outside the system.

2. The fragrance delivery system according to claim 1 wherein the thermoplastic elastomer block copolymer is a thermoplastic polybutylene-terephthalate copolymerized with at least one block of a material selected from the group consisting of polyether, polyester and polyesterether.

3. The fragrance delivery system according to claim 1 wherein the fragrance permeable plastic serves as a closure for the container.

4. The fragrance delivery system according to claim 1 wherein the thickness of the fragrance permeable plastic has a thickness ranging from 0.01 to 2 mm.

5. The fragrance delivery system according to claim 1 wherein the thickness of the fragrance permeable plastic has a thickness ranging from 0.2 to 1 mm.

6. The fragrance delivery system according to claim 1 wherein the relative amounts of high to low volatile perfume ingredients range from 100:1 to 1:2 by weight.

7. The fragrance delivery system according to claim 1 wherein the relative amounts of high to low volatile perfume ingredients range from 10:1 to 2:1 by weight.

8. The fragrance delivery system according to claim 1 wherein the relative amounts of high to low volatile perfume ingredients range from 100:1 to 1:2.

9. The fragrance delivery system according to claim 1 wherein the perfume ingredients within the reservoir compartments constitute from 5 to 100% of any liquid in these compartments.

10. The fragrance delivery system according to claim 1 wherein the perfume ingredients within the reservoir compartments constitute from 50 to 95% of any liquid in these compartments.

11. The fragrance delivery system according to claim 1 wherein the fragrance permeable plastic has not been impregnated with the perfume ingredients prior to being formed as the outer wall of the container.

12. The fragrance delivery system according to claim 1 wherein the Volume Resistivity ranges from $1\times10^{13}$ to $1\times10^{16}$ Ohms·cm.

13. The fragrance delivery system according to claim 1 wherein the Water Absorption ranges from 6 to 15%.

14. The fragrance delivery system according to claim 1 wherein the container is a capped bottle or a capped jar.

15. A method for simultaneously transmitting both high volatile perfume ingredients and low volatile perfume ingredients at a uniform and steady rate to space outside a plastic container, the method comprising:
   selecting a container with at least one reservoir compartment, the container comprising an outer wall at least partially being formed of a fragrance permeable plastic;
      i) the plastic being a thermoplastic elastomer block copolymer;
      ii) the plastic having a Volume Resistivity ranging from $1\times10^{12}$ to $1\times10^{20}$ Ohms·cm; and
      iii) the plastic having a Water Absorption ranging from 4 to 20%; and
   placing a fragrance composition within the at least one reservoir compartment, the composition being a mixture of: (1) high volatile perfume ingredients having a boiling point lower than 250° C.; and (2) low volatile perfume ingredients having a boiling point higher than 250° C.

* * * * *